United States Patent [19]

Keipi et al.

[11] Patent Number: 5,000,576

[45] Date of Patent: Mar. 19, 1991

[54] IDENTIFIER OF LOCATION OF TRAY

[75] Inventors: Antti Keipi; Jukka Tuunanen; Juha Koivisto, both of Helsinki, all of Finland

[73] Assignee: Labsytems Oy, Helsinki, Finland

[21] Appl. No.: 372,929

[22] Filed: Jun. 28, 1989

[30] Foreign Application Priority Data

Jul. 13, 1988 [FI] Finland ................................. 883330

[51] Int. Cl.$^5$ ...................... G01B 7/00; G01N 35/00; G01N 21/00

[52] U.S. Cl. .................................... 356/440; 33/1 M; 33/706; 324/686; 340/870.37

[58] Field of Search ............... 356/440; 324/658, 660, 324/661, 662, 686; 340/870.37; 33/1 M, 706, 784

[56] References Cited

U.S. PATENT DOCUMENTS 3,296,522  1/1967  Wolfendale ......................... 324/660
3,938,113  2/1976  Dobson et al. ................. 340/870.37
4,397,560  8/1983  Andresen ........................... 356/440

FOREIGN PATENT DOCUMENTS 185166  6/1986  European Pat. Off. .

*Primary Examiner*—Richard A. Rosenberger
*Attorney, Agent, or Firm*—Hopgood, Calimafde, Kalil, Blaustein & Judlowe

[57] ABSTRACT

The invention is related to a system of identification of the location of a matrix-like sample tray on a plane (2) in an equipment for the treatment of the samples. The sample tray is placed in a frame having an L-shaped electrically conductive piece (8). The equipment for the treatment comprises a number, corresponding to the number of vertical lines of the tray, electrically conductive strips (9), a number, corresponding to the number of horizontal lines, electrically conductive strips (10), and means for transmitting an electric signal to the strips of the vertical line and for receiving from the strips of the horizontal lines.

1 Claim, 1 Drawing Sheet

IDENTIFIER OF LOCATION OF TRAY

The invention is related to equipment for the treatment of liquid samples, such as a photometer, wherein the samples are placed in vessels provided in a particular sample disk or tray. In particular, the invention concerns a system by means of which it is possible to identify which vessel is in the treatment position at each particular time.

In photometric measurements, frequently a so-called microtiter tray is used as the measurement base, wherein there are a number of sample vessels placed in a matrix of, e.g., 8×12. The tray is shifted on the measurement plane of the photometer so that each vessel is in its turn placed below the measurement head of the photometer. Even though the measurement itself and the producing of output can be carried out as taking place automatically, there is still the problem how to identify the pit that is being measured at each particular time automatically.

In the U.S. Pat. No. 4,397,560 a method is described for identification of the location of a sample tray. Therein the sample tray is placed in a frame in which there are magnets of lengths equal to the lengths of the vertical and horizontal lines in the tray placed as perpendicular to one another. Underneath the measurement plane, there is a corresponding number of magnetic Hall detectors in two lines perpendicular to one another and spaced in a way corresponding to the spacing of the sample vessels. When a certain sample vessel is in the position of measurement, a signal is obtained to the magnetic detector corresponding both to the horizontal line concerned and to the vertical line concerned. The magnet rods must be quite precisely perpendicular to the detector lines. This requires particular care from the operator in devices in which the tray is shifted on the measurement plane by hand.

In the Published Patent Application FI 854471, an inductive system of identification of location is described. Therein there are two metal plates perpendicular to one another in a frame as well as the necessary number of inductive approach detectors in two perpendicular lines underneath the measurement plane. When a metal rod is placed above a detector, eddy currents are produced in the rod. On the other hand, the attenuation of said currents produces a current in the coil of the detector, the time of attenuation of said latter current being detected. A drawback is that the manufacture requires particular precision.

Now a system of identification in accordance with the patent claims has been invented.

An advantageous embodiment of the invention will be illustrated in more detail with the aid of the accompanying drawings.

Figure 1:
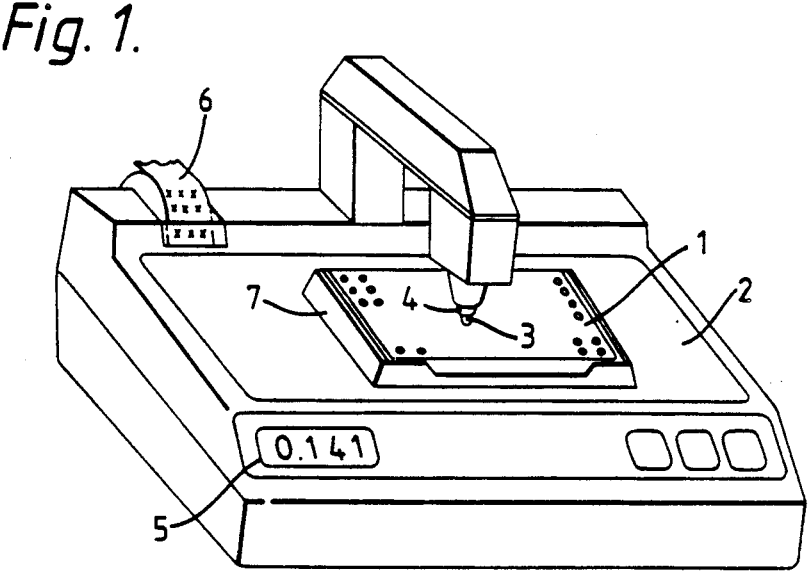
FIG. 1 shows a photometer, onto whose measurement plane a pit tray to be measured has been introduced in its measurement frame.
Figure 2:
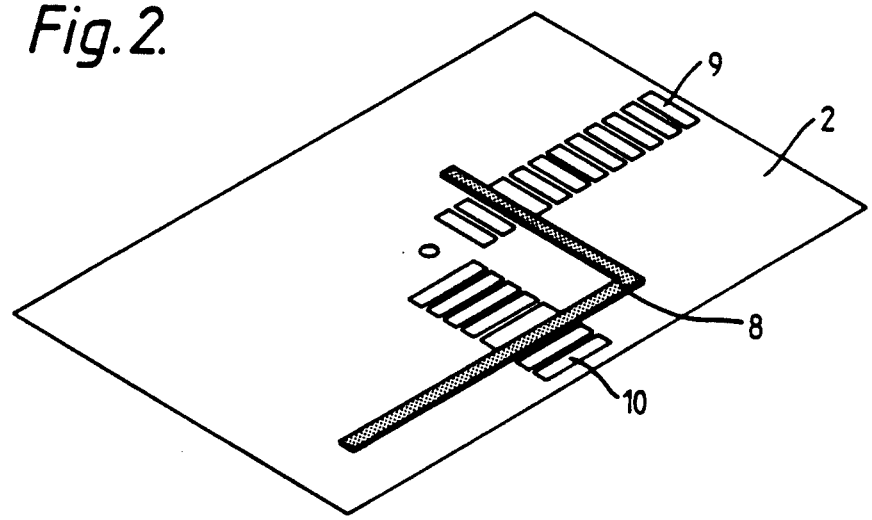
FIG. 2 is a schematical illustration of the main components of the system of identification of location.
Figure 3:
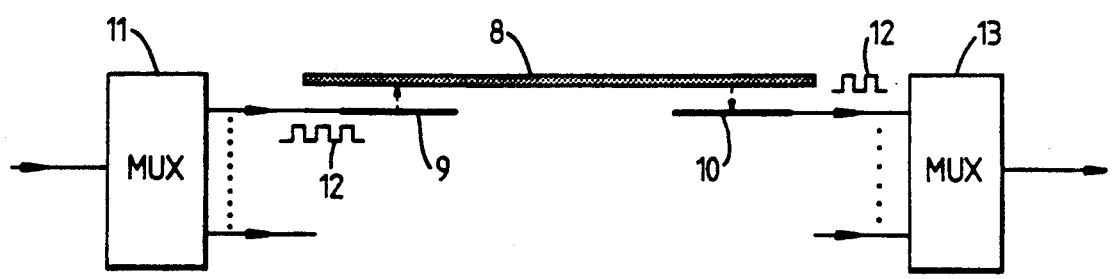
FIG. 3 shows the principle of operation of the system of identification.

In the photometer, a so-called microtiter tray 1 is used as the sample base, the substance to be studied being measured into the wells in said tray. The tray to be measured is placed onto the measurement plane 2 of the photometer so that the well 3 to be measured becomes placed facing the tip 4 of the measurement head. Said well is measured by means of photometric methods. The measurement result is displayed to the operator in the display unit 5, it is produced as an output by means of the printer 6 of the device, or it is transmitted by means of a peripheral device, e.g., to an external printer. The tray may be shifted freely on the measurement plane, so that the wells can be measured in any whatsoever. The locations of the wells in the tray are coded in the 96-well tray so that the 12 vertical lines are provided with current numbers 1 . . . 12 from the left to the right, and the 8 horizontal lines are provided with the letters A . . . H in the sequence from the top towards the bottom.

For the time of the measurement, the tray 1 to be measured is placed in a rectangular measurement frame 7. At its bottom angle, a thin L-shaped metal plate 8 parallel to the measurement plane is mounted. The shorter branch of the piece has a length equal to the length of the shorter side of the frame, and the longer branch a length equal to the length of the longer side of the frame.

Underneath the measurement plane 2, there are a number of metal strips 9 corresponding to the number of vertical lines and a number of metal strips 10 corresponding to the number of horizontal lines, placed at average distances from each other corresponding to the spacing of the wells in the tray. The metal strips 9 for the vertical line are somewhat shorter than the metal strips 10 for the horizontal line. The plate 8 and the metal strips 9 and 10 are placed in such a way that when a certain well is in the measurement position, the branches of the plate are placed facing the metal strips corresponding to the lines of wells. In this way a circuit has been formed in which there are two capacitors connected in series.

A multiplexer 11 passes an electric signal 12 alternatingly to each metal strip 9 for vertical line, which said signal is herein a square-wave-formed signal of about 20 kHz. From the metal strip 9 above which the branch of the plate 8 is placed the signal 12 is conducted through the other branch of the plate to the corresponding metal strip 10 for horizontal line, from which it is passed through the multiplexer 13 to detecting. The operation is controlled by a microprocessor.

The system described herein is reliable in operation and simple to construct. Moreover, it is composed of inexpensive and few components. As a matter of fact, the system does not include any detectors proper at all; only the metal strips are needed, which can be made directly onto a circuit card.

A corresponding system of identification may also be used, e.g., in a dosage unit.

What is claimed is:

1. System of identification of the location of a sample tray in an equipment for the treatment of liquid samples, provided with a frame (7) displaceable on a plane (2) and, in said frame, a sample tray (1), wherein there are sample vessels in a matrix consisting of vertical and horizontal lines, said sample vessels being passed to the treatment position each in its turn, which said system comprises in the frame, an L-shaped electrically conductive piece (8) parallel to the plane (2), one branch of said piece being of a length at least equal to the length of a vertical line in the sample tray and the other branch of said piece being of a length at least equal to the horizontal line in the sample tray, in the equipment for the treatment, in a line, a number, corresponding to the number of vertical lines, of electrically conductive strips (9) parallel to the plane at distances from each other corresponding to the average spacing of the wells in the vertical line, so that, when the branch of the piece in the frame that corresponds to a vertical line is placed facing a certain strip, the vessel in the corresponding vertical line being in a treatment position, in the equipment for the treatment, in a line, a number, corresponding to the number of horizontal lines, of electrically conductive strips (10) at distances from each other corresponding to the average spacing of the wells in the horizontal line, so that when the branch of the rod in the frame that corresponds to a horizontal line is placed facing a certain strip, the vessel in the corresponding horizontal line is in the treatment position, equipment (11) for transmission of an electric signal (12) alternatingly to each strip in a vertical line, as well as equipment (13) for receiving an electric signal alternatingly from each strip in a horizontal line.

* * * * *